United States Patent
Kabat

(10) Patent No.: US 6,603,030 B1
(45) Date of Patent: Aug. 5, 2003

(54) PROCESS FOR PRODUCING PHOSPHINEOXIDE VITAMIN D PRECURSORS

(75) Inventor: Marek Michal Kabat, Nutley, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/537,209

(22) Filed: Mar. 29, 2000

Related U.S. Application Data
(60) Provisional application No. 60/130,451, filed on Apr. 22, 1999.

(51) Int. Cl.[7] .................... C07C 401/00; A61K 31/59
(52) U.S. Cl. ......................... 552/653; 552/653
(58) Field of Search .............. 568/8; 552/653; 514/167

(56) References Cited

U.S. PATENT DOCUMENTS

| | | | | |
|---|---|---|---|---|
| 5,830,885 A | | 11/1998 | Posner | ........ 514/167 |
| 6,153,605 A | * | 11/2000 | Barbier et al. | ........ 514/167 |

FOREIGN PATENT DOCUMENTS

| | | |
|---|---|---|
| EP | 0516 410 | 12/1992 |
| EP | 808833 | 11/1997 |
| JP | 5279283 | 10/1993 |
| WO | 96 03994 | 2/1996 |
| WO | WO 9851663 | 11/1998 |
| WO | 99 31055 | 6/1999 |

OTHER PUBLICATIONS

Posner, G. et al., J. Org. Chem., 62, pp. 3299–3314 (1997).
Baggiolini E. et al., J. Org. Chem., 51, pp. 3098–3108 (1986).

* cited by examiner

*Primary Examiner*—Sabiha Qazi
(74) *Attorney, Agent, or Firm*—George W. Johnston; John P. Parise

(57) ABSTRACT

A process for producing a compound of the formula:

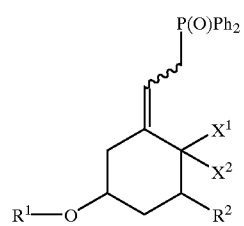

1 where Ph is phenyl, $X^1$ and $X^2$ are both hydrogen or $X^1$ and $X^2$ taken together are $CH_2$, $R^1$ is a protecting group, $R^2$ is fluorine, hydrogen, or $OR^3$, where $R^3$ is a protecting group, and the squiggly line represents a bond that results in the adjacent double bond being in either the E or Z configuration, involves:

(a) chlorinating a compound of the formula:

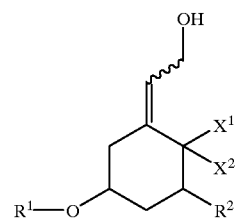

2 where $X^1$, $X^2$, $R^1$, $R^2$, and the squiggly line are as above, using triphosgene in the presence of an organic base to obtain the compound of the formula:

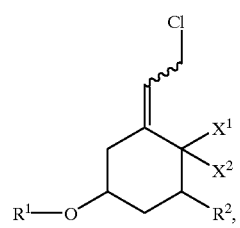

3 where $X^1$, $X^2$, $R^1$, $R^2$, and the squiggly line are as above; and (b) reacting the compound of formula 3 with a salt of diphenyl phosphine oxide to obtain the compound of formula 1. Each of the above steps (a) and (b) are individually useful.

14 Claims, No Drawings

PROCESS FOR PRODUCING PHOSPHINEOXIDE VITAMIN D PRECURSORS

This application claims priority of prior provisional application Ser. No. 60/130,451 filed on Apr. 22, 1999 under 35 USC §119 (e).

BACKGROUND OF THE INVENTION

Vitamin D analogs, such as 1α-fluoro-25-hydroxy-16-23E-diene-26,27-bishomo-20-epi-cholecalciferol, 1,25-dihydroxy-16-ene-23-yne-26,27-bishomo-19-nor-20-epi-cholecalciferol, 1α, 25-dihydroxy-18-norvitamin D3, 1α, 25-dihydroxy-18,19-dinorvitamin D3, 1α-fluoro-25-hydroxycholecalciferol, and 1α-fluoro-25-hydroxyergocalciferol, are known to have pharmaceutical activity and are useful for treating various conditions, such as psoriasis and neoplastic disease.

A key phosphine oxide compound of formula 1 below is used in the efficient synthesis of such vitamin D analogues and provides the A ring of the vitamin. Certain species of Compound 1 are known to be valuable intermediates in the synthesis of the mentioned pharmacologically active vitamin D analogues (see for example EP Publication No. 0 808 833). The remaining species of Compound 1 can be modified to be useful in the above processes or can be used for producing other vitamin D analogues. Known processes for making this intermediate of Compound 1 typically result in low yields. However, the subject invention provides a process to produce the desired intermediate in high yield.

SUMMARY OF THE INVENTION

The subject invention provides a process for producing a compound of the formula:

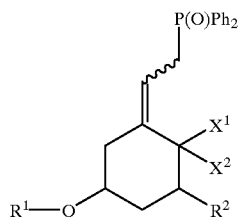

where Ph is phenyl, $X^1$ and $X^2$ are both hydrogen or $X^1$ and $X^2$ taken together are $CH_2$, $R^1$ is a protecting group, $R^2$ is fluorine, hydrogen, or $OR^3$, where $R^3$ is a protecting group, and the squiggly line represents a bond that results in the adjacent double bond being in either the E or Z configuration. This process comprises chlorinating a compound of the formula:

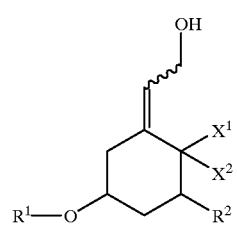

where $X^1$, $X^2$, $R^1$, $R^2$, and the squiggly line are as above, using triphosgene in the presence of an organic base to obtain the compound of the formula:

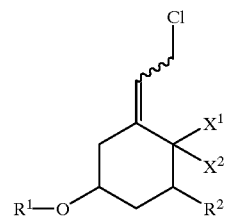

where $X^1$, $X^2$, $R^1$, $R^2$, and the squiggly line are as above. The compound of formula 3 is then reacted with a salt of diphenyl phosphine oxide to obtain the compound of formula 1.

DETAILED DESCRIPTION OF THE INVENTION

The invention will now be described in terms of its preferred embodiments. These embodiments are set forth to aid in understanding the invention but are not to be construed as limiting.

The invention is an improved process for producing a compound of formula 1 ("Compound 1"). This process involves chlorinating a compound of formula 2 ("Compound 2") using triphosgene as the chlorine source in the presence of an organic base to obtain the compound of formula 3 ("Compound 3"). The chlorine in Compound 3 is replaced by phosphine oxide using a salt of diphenyl phosphine oxide that can be formed in situ, to obtain Compound 1. The structures of Compounds 1–3 are set forth below.

Compound 1 is a compound of the formula:

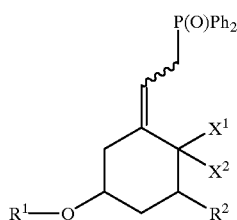

where Ph is phenyl, $X^1$ and $X^2$ are both hydrogen or $X^1$ and $X^2$ taken together are $CH_2$, $R^1$ is a protecting group, $R^2$ is fluorine, hydrogen, or $OR^3$, where $R^3$ is a protecting group, and the squiggly line represents a bond that results in the adjacent double bond being in either the E or Z configuration. For clarity, the squiggly line is shorthand for the following two configurations:

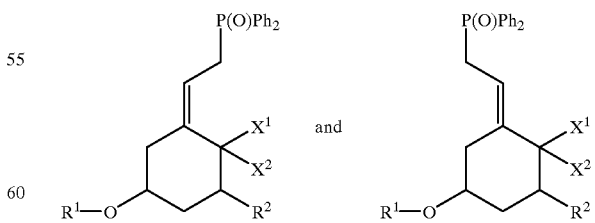

Since Compound 1 can be used in numerous synthetic pathways for producing vitamin D analogs, the bonds between the ring carbons and the $OR^1$ substituent and $R^2$ can be in either the α or β configuration as needed for the final synthesis.

Compound 1 is produced by chlorinating Compound 2 of the formula:

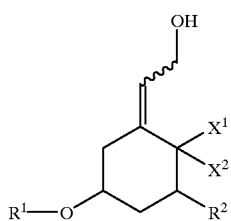

where $X^1$ and $X^2$, $R^1$ and $R^2$, and the squiggly line are as defined for Compound 1. Compound 2 is reacted with triphosgene in the presence of an organic base to obtain Compound 3 where Ph, $X^1$ and $X^2$, $R^1$ and $R^2$, and the squiggly line are as defined for Compound 1.

Many species of Compound 2 are known. See for example, Perlman et al., *Novel synthesis of 19-nor-vitamin D compounds,* Tetrahedron Lett., 32(52): 7663–6 (1991), Courtney et al., *Asymmetric synthesis of a key ring A synthon for 1α-hydroxy-19-nor vitamin D,* Tetrahedron Lett., 39(21): 3363–3366 (1998), Shiuey et al. *Total synthesis of 1α-fluoro-25-hydroxycholecalciferol and -ergocalciferol.,* J. Org. Chem. 55(1): 243-7 (1990), Reddy, *Synthesis and activity of 3-epi vitamin D3 compounds for use in treatment of disorders involving aberrant activity of hyperproliferative skin, parathyroid, and bone cells.,* PCT Publication No. WO 9851663, Sotojima, *Preparation of cyclohexylideneethanol derivatives as intermediates for 1α-hydroxy- and 1α, 25-dihydroxyvitamin D3,* JP Kokai No. 05279283, Baggiolini et al., *Stereoselective total synthesis of 1α, 25-dihydroxycholecalciferoL,* J. Am. Chem. Soc., 104(10): 2945-8 (1982). The remaining species of Compound 2 can be produced from these known compounds using procedures known in the art. Such production is well within the skill of the artisan.

Compound 3 has the formula:

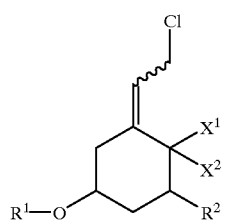

where $X^1$ and $X^2$, $R^1$ and $R^2$, and the squiggly line are as defined for Compound 1. Compound 3 is then reacted with a salt of diphenyl phosphine oxide, to obtain Compound 1.

In any of the above processes of this invention, $R^1$ can be any appropriate protecting group. The choice of an appropriate protecting group is within the skill of the artisan. By hydroxy protecting group is meant any standard compound for protecting a hydroxy group during a chemical reaction (such that the hydroxy group is easily reinstated), specifically during acidic or basic hydrolysis. However, a silyl protecting group, such as tert-butyl dimethyl silyl ("TBS") is preferred.

$R^2$ can be fluorine, hydrogen, or a protected hydroxy group. A protected hydroxy group is a group in which oxygen binds to the ring and is protected by a protecting group. As above, the choice of an appropriate protecting group is within the skill of the artisan. Preferred protected hydroxy groups include silyl protected hydroxy groups, such as hydroxy protected by TBS. The use of a TBS protected hydroxy group results in $R^2$ being tert-butyl dimethyl silyl oxide ("TBSO"). For any compound of this invention, $R^1$ and $R^2$ may use the same or different hydroxy protecting groups.

The salts of diphenyl phosphine oxide that can be used in the inventive process include the sodium, lithium, and potassium salts. However, the sodium salt is preferred. In a preferred process, $R^1$ is TBS and $R^2$ is fluorine or TBSO. For the chlorination of Compound 2, a preferred amount of triphosgene is about one-half (½) mole relative to one (1) mole of Compound 2. Either pyridine or triethylamine may be added to the reaction. For either one, the preferred amount is 2 equivalents.

In preferred processes of this invention, $R^1$ is TBS, $R^2$ is $OR^3$, and $R^3$ is TBS. In other preferred processes, $R^1$ is TBS and $R^2$ is fluorine. In yet other preferred processes, $R^1$ is TBS and $R^2$ is hydrogen. In the subject invention, Compounds 1, 2, and 3 can have the $P(O)(Ph)_2$, OH, and Cl, respectively, in either the cis or trans position. In any of these compounds, $R^1$ and $R^2$ may be present above (◊) or below (◊) the plane of the cyclohexane ring to which they are attached. Both may be above, both may be below, or one may be above and the other may be below.

Reaction Scheme

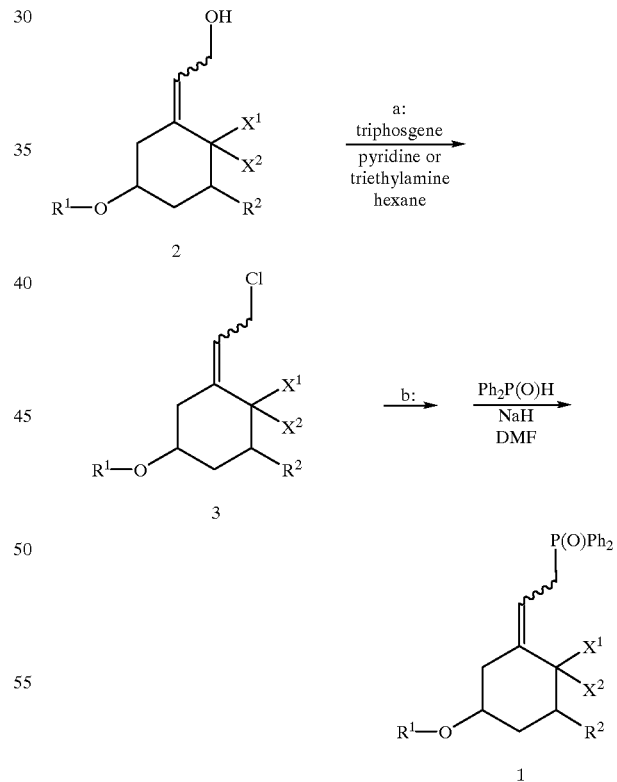

Compound 3 is obtained from Compound 2 by chlorinating the allylic alcohol of Compound 2 to the allylic chloride in Compound 3. This chlorinating is performed in and organic solvent, preferably an aprotic solvent such as hexane. For each mole of Compound 2, one-half (½) mole or more of triphosgene is used as the chlorine source. At least 2 equivalents of an organic base, preferably an aprotic amine base such as pyridine, or preferably triethylamine, should be included. Temperature is not critical and may range between −30° C. and 50° C. However, a temperature around 0° C. is preferred.

Compound 1 is obtained from Compound 3 by replacing the chlorine with phosphine oxide. Results are obtained by using an alkali metal salt of diphenylphosphine oxide, preferably the sodium salt. Other acceptable alkali metal salts include lithium and potassium salts. Such alkali metal salts of diphenylphosphine oxide are preferably generated in situ by reacting diphenylphosphine oxide with an alkali metal hydride. Excess reagent should be avoided to limit formation of by-products.

The Examples that follow are intended to further illustrate the invention without limiting it in any way.

EXAMPLES

Example 1 Preparation of (Z)-(1 S,5R)-1,5-bis-(tert-butyl-dimethyl-silanyloxy)-3-(2-chloro-ethylidene)-2-methylene-cyclohexane

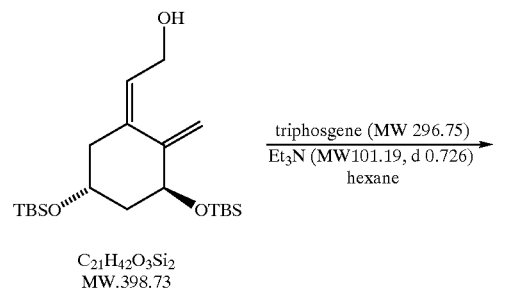

A 500 mL, three-necked, round-boftomed flask equipped with a thermometer, mechanical stirrer, dropping funnel and nitrogen bubbler was charged with 18.2 g (45.6 mmol) of the precursor and 250 mL of hexane. To the resulting solution was added 6.76 g of triphosgene (22.8 mmol.) in one portion. The mixture was cooled with an ice-water bath, and, after a clear solution resulted, 22.3 mL (160 mmol) of triethylamine was added dropwise over 10 min with vigorous stirring. After stirring at 5° C. for 20 min, the cooling bath was removed and the resulting thick suspension was stirred at room temperature for 1 h. TLC analysis indicated complete reaction. The reaction mixture was diluted with 150 mL of hexane and washed with 2×250 mL=500 mL of ice-cold 0.25N hydrochloric acid and 2×250 mL=500 mL of water. The combined aqueous layers were back-extracted with 2×100 mL=200 mL of hexane. All the organic layers were combined, washed with 150 mL of saturated sodium chloride solution, dried over magnesium sulfate and concentrated to dryness at 30° C. under reduced pressure. The residual mixture was then purged with nitrogen for 15 min to give 19.2 g of (Z)-(1 S,5R)-1,5-bis-(tert-butyl-dimethyl-silanyloxy)-3-(2-chloro-ethylidene)-2-methylene-cyclohexane as a slightly hazy, yellow oil. This material solidified upon storing overnight in a freezer and was directly used to the next step without further purification.

In-process controls: NMR (CDCl$_3$) and TLC (9:1 hexane:ethyl acetate; short-wave UV detection and PMA stain; R$^f$ precursor=0.2 and R$^f$ final product=0.6)

Example 2 Preparation of 3S-(3α,5β,Z)-2-2-2-methylene-bis(1,1 -dimethylethyl)dimethyl-silyl-oxy-cyclohexylidene-ethyl-diphenyl phosphine oxide

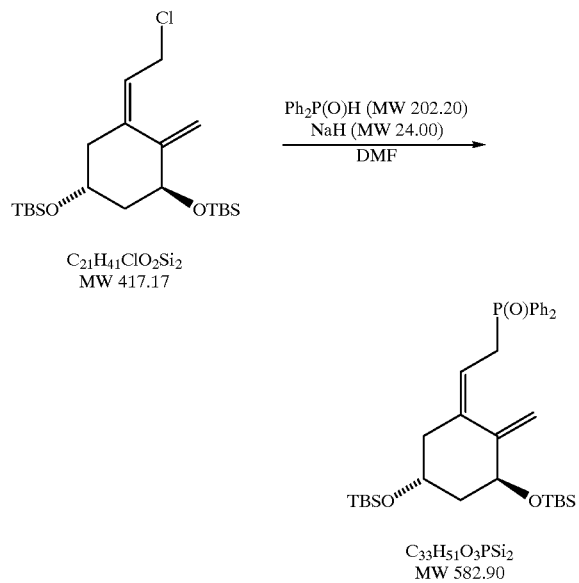

A 500 mL, three-necked, round-boftomed flask equipped with a thermometer, magnetic stirrer, dropping funnel and nitrogen bubbler was charged with 2.02 g (50.6 mmol) of sodium hydride (60% dispersion in mineral oil) and 170 mL of DMF. Then, 10.2 g (50.6 mmol) of diphenylphosphine oxide was added in one portion. Gas evolution was observed and a mild exotherm ensued that raised the temperature of the mixture to 28° C. The mixture was stirred at room temperature for 50 min to give a slightly cloudy, yellow solution. After cooling the solution to −45° C. with a dry-ice acetone bath, a solution of 19.2 g (45.2 mmol, theoretical) of precursor in 70 mL of DMF was added dropwise over 25 min, while maintaining the reaction temperature below −35° C. The funnel was rinsed with 10 mL of DMF and the rinse was added to the mixture. The reaction mixture was stirred at −30 to −35° C. for 1.5 h, then allowed to warm to 0° C. and stirred at that temperature for 30 min. TLC analysis indicated complete reaction. The reaction mixture was diluted with 500 mL of diethyl ether and washed with 2×200 mL=400 mL of water. The combined aqueous layers were back-extracted with 2×150 mL=300 mL
of diethyl ether and these back-extracts were combined and washed with 2×200 mL=400 mL
of water. All the organic layers were combined, dried over magnesium sulfate and concentrated to dryness at 35° C. under reduced pressure. The resulting residue was further dried under high vacuum to give 26.2 g of a cloudy, yellow oil. This material was dissolved in
50 mL of hexane and the resulting solution was filtered though
150 g of TLC silica gel. The silica gel plug was then washed with
200 mL of hexane,
1 L of 9:1 hexane:ethyl acetate,
1 L of 8:2 hexane:ethyl acetate and
1 L of 7:3 hexane:ethyl acetate. The appropriate fractions were combined and concentrated to dryness at 35° C. under reduced pressure, then dried under high vacuum overnight to give 22.3 g (83.7% over two steps) of final product as a colorless foam.
In-process controls: NMR (CDCl$_3$) and TLCs (9:1 hexane:ethyl acetate; short-wave UV detection and PMA stain; R$^f$ precursor=0.6, 1:1 hexane:ethyl acetate; short-wave UV detection and PMA stain; R$^f$ precursor=0.95 and R$^f$ final product=0.45)

Example 3 Preparation of [[(1R,3Z,5S)-3-(2-chloroethylidine)-5-fluoro-4-methylenecyclohexyl]oxy](1,1-dimethylethyl)dimethyl silane

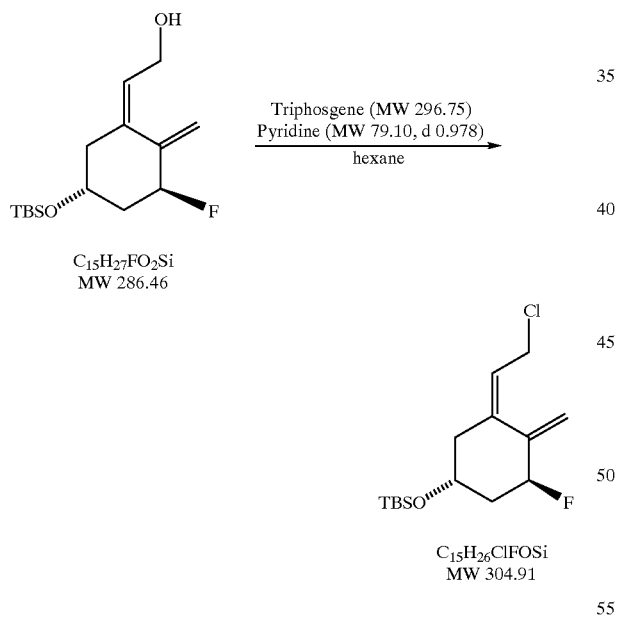

A 500 mL, three-necked, round-bottomed flask equipped with a thermometer, magnetic stirrer, dropping funnel with nitrogen inlet tube and outlet bubbler was charged with
8.07 g (28.2 mmol) of precursor,
150 mL of hexane and
4.18 g (14.1 mmol) of triphosgene. The solution was cooled to 0° C. with an ice-acetone bath and a solution of
4.50 mL (55.6 mmol) of pyridine in
20 mL of hexane was added over 30 min. After stirring at 0° C. for 30 min, the cooling bath was removed and the resulting pale-yellow reaction mixture was stirred at room temperature for 30 min. Then, the reaction mixture was diluted with
250 mL of hexane, washed with 3×200 mL=600 mL
of saturated copper (II) sulfate solution. The combined aqueous layers were extracted with 2×100 mL=200 mL
of hexane. The organic layers were combined, dried over magnesium sulfate and concentrated to dryness on a rotary evaporator to give 9.0 g (overweight) of final product as a pale yellow oil
In-process controls: NMR (CDCl$_3$) and TLC (4:1 hexane:ethyl acetate; short-wave UV detection and PMA stain; R$^f$ precursor=0.3 and R$^f$ final product=0.9).

Example 4 Preparation of (S-trans)-1-fluoro-5-[[dimethyl(1,1-dimethylethyl)silyl]oxy]-2-methenyl-3-[(diphenylphosphinyl)ethylidene]cyclohexane

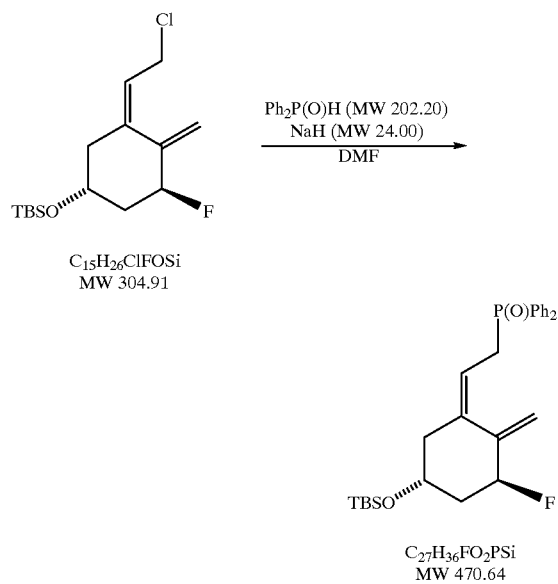

A 100 mL, three-necked, round-bottomed flask equipped with a thermometer, magnetic stirrer, dropping funnel with nitrogen inlet tube and outlet bubbler was charged with
50 mL of DMF and
1.33 g (33.1 mmol) of sodium hydride (60% dispersion in mineral oil). While cooling with a water bath (10° C.),
6.70 g (33.1 mmol) of diphenylphosphine oxide was added in small portions over 15 min. The water bath was removed and the resulting yellow solution was stirred at room temperature for 30 min. After cooling to −60° C. with a dry-ice acetone bath, a solution of
9.0 g (28.2 mmol, in theory) of precursor in
20 mL DMF was added dropwise, via a syringe, over 15 min, while maintaining the temperature of the reaction mixture below −50° C. The reaction mixture was stirred at −60° C. for 2 h, then allowed to warm to room temperature over 1 h. The reaction mixture was diluted with
600 mL of diethyl ether and washed with 3×200 mL=600 mL
of water. The combined aqueous layers were extracted with
200 mL of diethyl ether. The organic layers were combined, dried over magnesium sulfate and concentrated under reduced pressure to give a white solid. This crude product was recrystallized from 25 mL of diisopropyl ether. The resulting solid was collected by filtration, washed with 5 mL of cold diisopropyl ether and dried under high vacuum to give 7.93 g (59.8%) of final product as a white solid. The mother liquor was concentrated and the residue was subjected to chromatography on silica gel, eluting with 7:3-1:1 hexane:ethyl acetate. The appropriate fractions were combined and concentrated to dryness to give 2.22 g (16.7%) of final product. Thus, the total yield of final product was 10.1 g (76.5% overall from precursor).

In-process controls: NMR ($CDCl_3$) and TLC (1:1 hexane:ethyl acetate; short-wave UV detection and PMA stain; $R_f$ precursor=1.0 and $R_f$ final product=0.28).

The subject invention has been described in terms of its preferred embodiments. Upon reading the present specification, various alternative embodiments will become obvious to the skilled artisan. These variations are to be considered within the scope and spirit of the invention that is only to be limited by the claims that follow and their equivalents.

What is claimed is:

1. A process for producing a compound of the formula:

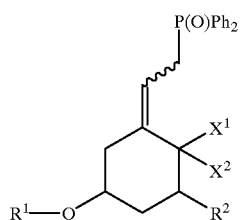

where Ph is phenyl, $X^1$ and $X^2$ are both hydrogen or $X^1$ and $X^2$ taken together are $CH_2$, $R^1$ is a protecting group, $R^2$ is fluorine, hydrogen, or $OR^3$, where $R^3$ is a protecting group, and the squiggly line represents a bond that results in the adjacent double bond being in either the E or Z configuration, which comprises:

reacting a compound of the formula:

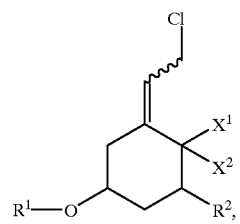

where $X^1$, $X^2$, $R^1$, $R^2$, and the squiggly line are as above with a salt of diphenyl phosphine oxide to obtain the compound of formula 1.

2. The process of claim 1, wherein $R^1$ is a silyl protecting group.

3. The process of claim 1, wherein $R^1$ is a tert-butyl dimethyl silyl group.

4. The process of claim 1, wherein $R^2$ is fluorine.

5. The process of claim 1, wherein $R^2$ is tert-butyl dimethyl silyl oxide.

6. The process of claim 1, wherein $R^2$ is fluorine or $OR^3$, and $R^3$ is tert-butyl dimethyl silyl.

7. The process of claim 1, wherein $X^1$ and $X^2$ taken together are $CH_2$.

8. The process of claim 1, wherein the reacting is performed using a salt of diphenyl phosphine oxide that has been generated in situ by reacting diphenyl phosphine oxide with a alkali metal hydride.

9. The process of claim 1, wherein the reacting is performed using the sodium salt of diphenyl phosphine oxide.

10. The process of claim 9, wherein the reacting is performed using the sodium salt of diphenyl phosphine oxide that has been generated in situ by reacting diphenyl phosphine oxide with sodium hydride.

11. The process of claim 1, wherein the reacting is performed in an organic solvent.

12. The process of claim 11, wherein the reacting of step (b) is performed in DMF.

13. The process of claim 1, wherein the reacting is performed at a temperature of from about −80° C. to about 50° C.

14. The process of claim 13, wherein the reacting is performed at a temperature of about −60° C.

* * * * *

UNITED STATES PATENT AND TRADEMARK OFFICE
CERTIFICATE OF CORRECTION

PATENT NO.    : 6,603,030 B1                                               Page 1 of 1
DATED         : August 5, 2003
INVENTOR(S)   : Marek Michal Kabat It is certified that error appears in the above-identified patent and that said Letters Patent is hereby corrected as shown below:

<u>Title page,</u>
Item [73], Assignee, delete "Hoffman-La Roche Inc., Nutley, NJ (US)" and insert
-- Hoffmann-La Roche Inc., Nutley, NJ (US) --.

Signed and Sealed this

Twentieth Day of January, 2004

JON W. DUDAS
*Acting Director of the United States Patent and Trademark Office*